United States Patent [19]

Elson

[11] Patent Number: 5,510,391

[45] Date of Patent: Apr. 23, 1996

[54] METHOD OF TREATING BLOOD VESSEL DISORDERS OF THE SKIN USING VITAMIN K

[75] Inventor: Melvin L. Elson, Nashville, Tenn.

[73] Assignee: Mayapple Holdings, LLC, Burns, Tenn.

[21] Appl. No.: 140,615

[22] Filed: Oct. 22, 1993

[51] Int. Cl.[6] .................................................. A61K 31/12
[52] U.S. Cl. .................................................. 514/681
[58] Field of Search .............................................. 514/681

[56] References Cited

U.S. PATENT DOCUMENTS 5,162,377  11/1992  Kakoki et al. ........................... 514/772
5,180,747   1/1993  Matsuda et al. ......................... 514/681

OTHER PUBLICATIONS

Cosmetic and Drug Preservation, Principles and Practice, Published by Marcel Dekker, Inc. NY in 1984 (pp. 144 and 616).

Primary Examiner—Raymond Henley, III
Attorney, Agent, or Firm—Waddey & Patterson; I. C. Waddey, Jr.; Arles A. Taylor, Jr.

[57] ABSTRACT

A vitamin K mixture is used in a topical application for the treatment of blood vessel disorders of the skin which include, but are not limited to, actinic and iatrogenic purpura, lentigines and other vascular problems of the skin and subcutaneous tissue. The formulation of the mixture includes a number of the following substances: vitamin K, 95% ethyl alcohol SD40, isopropyl alcohol 99%, benzyl alcohol, lecithin granules, isopropyl palmitate NF, propyl paraben, methyl paraben, Pluronic F-127 NF, Dowicil 200 and preserved water. The concentrations of the substituent compounds vary in the different formulations of the vitamin K cream.

8 Claims, 4 Drawing Sheets

METHOD OF TREATING BLOOD VESSEL DISORDERS OF THE SKIN USING VITAMIN K

BACKGROUND OF THE INVENTION

Treatment of vascular problems of the skin and subcutaneous tissue is a major area of dermatological therapy given the increasingly large aging population. A number of dermatological conditions which involve blood vessel disorders of the skin and skin disorders caused by photoaging include actinic and iatrogenic purpura, lentigines, telangiectasias of the face, spider angiomas, spider veins of the face, spider veins of the legs as well as other vascular problems of the skin and subcutaneous tissue. There is currently no treatment for actinic or iatrogenic purpura and the only treatment for spider veins is surgical. Thus, treatments for these various blood vessel disorders of the skin are clearly limited at best.

SUMMARY OF THE INVENTION

The present invention relates to a new composition and method of treating blood vessel disorders of the skin using vitamin K. I have discovered that disorders of the skin which respond to treatment by use of vitamin K include but are not limited to actinic and iatrogenic purpura, lentigines, telangiectasias of the face, spider angiomas, spider veins of the face, spider veins of the legs and other vascular problems of the skin and subcutaneous tissue.

Vitamin K is necessary for the production via the liver of active prothrombin (Factor II), proconvertin (Factor VII), plasma thromboplastin component (Factor IX) and Stuart Factor X. Vitamin K is found in the form of vitamin K-1 (produced by green leafy vegetables) and vitamin K-2 (produced by gastrointestinal bacteria). In addition, vitamin K analogs have been synthesized and currently include vitamins K-3, K-4, K-5, K-6 and K-7. Naturally occurring in many foods, especially green leafy vegetables, the minimum daily requirement for vitamin K-1 has not been established. Most data accumulated regarding hypovitaminosis K is in the newborn. Guillamoont, Sann et al reported in the Journal of Pediatric Gastroenterology and Nutrition that hepatic phylloquinone storage at birth was poor (<1 microgram) and that the newborn infant might be in a situation of potential deficiency and prophylactic administration of the vitamin would be essential in neonatal surgical situations to prevent excessive bleeding. This deficiency in the new born period is due to two factors—the only sources are green leafy vegetables (for vitamin K1) and synthesis (of vitamin K2) by gastrointestinal bacteria, which are not yet established in the newborn.

Phytonadione (Vitamin K1; 2-methyl-3-phytyl-1-4-naphthoquinone)is a vitamin, which is clear yellow, viscous and odorless. It is insoluble in water and slightly soluble in alcohol. Its empirical formula is $C_{31}H_{46}O_2$ and its structural formula is

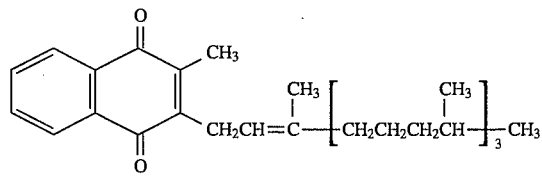

Clinical uses of Vitamin K in the past have been directly linked with its ability to influence coagulation rather than any deficiency disease process, primarily in anticoagulant-induced prothrombin deficiency caused by coumarin or indanedione derivatives, hypoprothrombinemia due to antibacterial therapy, factors limiting absorption, or salicylism.

Human skin undergoes a great deal of changes as it ages—both intrinsic and extrinsic. Part of these changes occur in the vascular system. Aged dermis is relatively avascular. There is an absolute loss of vertical capillary loops in the papillary dermis as well as a decrease in the number of veil cells (fibroblast like cells that deposit basement membrane materials around vessels in response to vascular insults). In addition to these intrinsic changes, photo aging also affects the vasculature of the skin in that changes in the collagen supporting the vessels create an environment in which the vessels break, become dead end vessels, decrease in size and become fragile. The least bit of trauma induces either purpura or an erosion of the surface.

The use of vitamin K parenterally has been standard therapy in surgery and internal medicine for many decades. It has also been indicated in the past that the ingestion of foods high in vitamin K content could decrease excessive menstrual flow and influence other bleeding diatheses.

Although the use of topical tretinoin and the alpha hydroxy acids may significantly improve photoaged skin in terms of both color and texture and studies have shown a re-establishment of some of the vasculature after tretinoin, no treatment has been effective in the alleviation of actinic purpura.

In addition, there are a number of clinical situations in which there is increased bleeding diathesis into the skin, such as steroidal therapy—both systemic and topical as well as salicylates, and many disease states. These situations can be very disconcerting to the patient.

With the foregoing summary of my invention in mind, it is an object of this invention to provide a method of treatment of various blood vessel disorders of the skin using vitamin K in addition to providing a formula for a vitamin K cream to treat various blood vessel disorders of the skin.

It is an additional object of this invention to provided a method for treatment of actinic and iatrogenic purpura and lentigines using vitamin K, as well as formula for a vitamin K cream to treat actinic and iatrogenic purpura and lentigines.

It is a further object of this invention that the method developed in this application will enable topical vitamin K treatment of superficial vascular disorders of the skin. One noteworthy advantage of the present use of a vitamin K cream formulation is the ease of treatment. Currently, surgery is the only method of treatment for spider veins. Surgery is clearly a less desirable procedure than topical application of a cream. Not only does the application of a cream provide an easier and less traumatic method of treatment, it will also reduce the cost involved in treating this medical problem. In addition, there are no known treatments for other known vascular disorders of the skin.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DESCRIPTION OF THE PREFERRED EMBODIMENT

Figure 1:
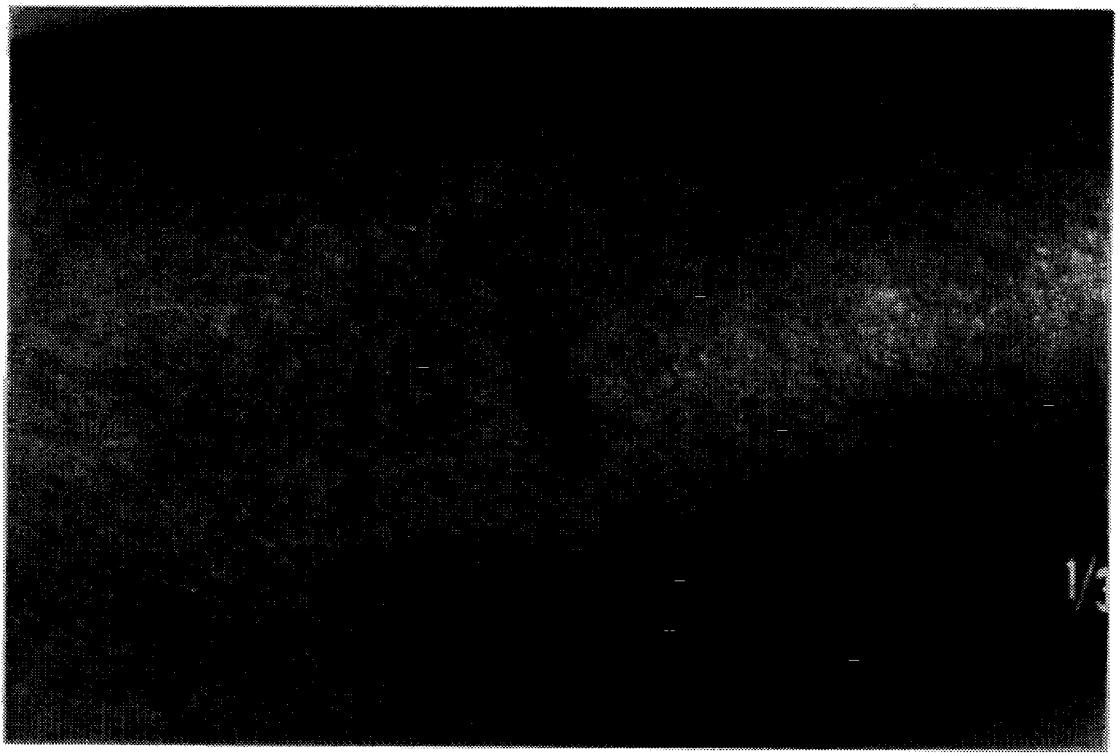
FIG. 1 is a photograph of iatrogenic purpura on a patient's right arm before treatment with 0.8% to 1% vitamin K-1 cream.

The present invention provides a method of treatment of vascular disorders of the skin by using a vitamin K cream and a formula for the composition of the cream itself. The present invention comprises the use of vitamin K in the form of either vitamin K-1 (Phytonadione) or vitamin K-2 in a topical formulation for the treatment of actinic and iatrogenic purpura among other disorders of the skin. The use of a topical vitamin K-1 containing cream is effective in the treatment of actinic and iatrogenic purpura and lentigines, among other disorders of the skin.

My composition containing 1% vitamin K-1 in a unique cream base system delivers vitamin K into the skin and appears to have an influence on the disappearance of extravascular blood, as well as decreasing the incidence of purpura, when compared to its base, when used on a twice daily basis. No benefit was obtained on the appearance of intact vessels of the skin when comparing the active to the placebo agent. There appears to be no effect on the vessel themselves, only on leaking vessels and blood already outside the dermal vascular system with this particular formulation and concentration.

VITAMIN K-1 CREAM-5%

A preferred embodiment of the cream of the present invention comprises the compounding formula of a vitamin K-1 cream-5%. To mix a 100 gram quantity of the vitamin K-1 5% cream, it is necessary to mix 5 grams of Phytonadione (Roche Vimmine and Fine Chemicals, Hoffman-LaRoche Inc., Belvidere, N.J.), 5 ml of 95% ethyl alcohol SD40, 2 ml of benzyl alcohol (Carrubba, Inc., Milford, Conn.), 10 grams of lecithin granules (American Lecithin Co., Danbury, Conn.), 10 ml of isopropyl palmitate NF (Amerchol corp., Edison, N.J.), and 20 grams Pluronic F-127, NF (BASF corp., Parsippany, N.J.). The mixture is then QS'ed to 100 grams with preserved water. In the above preferred embodiment, Pluronic F-127, NF is a known surfactant.

VITAMIN K-1 CREAM-1%

A preferred embodiment of the cream of the present invention comprises the compounding formula of a vitamin K-1 cream-1%. To mix a 100 gram quantity of the vitamin K-1 cream-1%, it is necessary to mix 1 gram of Phytonadione (Roche Vitamine and Fine Chemical, Hoffman-LaRoche Inc., Belvidere, N.J.), 2.42. ml of 99% isopropyl alcohol (Ruger Chemical Co., Irvington, N.J.), 1.73 ml of benzyl alcohol (Carrubba, Inc., Milford, Conn.), 8.26 grams of lecithin granules (American Lecithin Co., Danbury, Conn.), 7.44 ml of isopropyl palmitate NF (Amerchol Corp., Edison , N.J.), and 16.53 grams Pluronic F-127, JF (BASF Corp., Parsippany, N.J.), 0.04 gram propyl paraben (Ruger Chemical Corp., Irvington, N.J.), 0.13 gram methyl paraben (Ruger Chemical Corp., Irvington, N.J.), 0.04 gram Dowicil 200 (Ruger Chemical Corp., Irvington, N.J.) and 62.41 ml distilled water. In the above preferred embodiment, Pluronic F-127, NF is a known surfactant.

CASE STUDY OF THE TREATMENT WITH VITAMIN K-1 CREAM (0.8% TO 1%)

The initial study of the effects of a vitamin K-1 cream used in treatment of blood vessel disorders of the skin and skin disorders caused by photoaging involved use of a cream of 0.8% to 1% concentration of vitamin K-1 in June, 1993 on actinic and iatrogenic purpura among other skin disorders. Twelve patients were selected to apply this medication twice daily and all noticeably benefited from its use.

The twelve patients who were chosen to participate in the study had purpura on the hands and arms. Patients for easy bruising were solicited by newspaper as well as from hematologists and rheumatologists. Two creams were prepared, one with vitamin K-1 (0.8% to 1% ) and one identical except with no vitamin K and added yellow color to make the agents appear the same. Because of the size of the vitamin K molecule, it was necessary to develop a unique delivery system to ensure penetration.

At the commencement of this study, patients were evaluated and photographed. Informed consent was obtained from the patients. Patients were instructed according to the following protocol:

1. Apply Cream A to the back of the right hand and the lower arm with the left hand using an amount the size of a pea.

2. Apply Cream B to the back of the left hand and the lower arm with the right hand using an amount the size of a pea.

3. Use no moisturizers, no glycolic acid, no Retin A and no topical medications on the hands during the period of this study.

4. Return in 2,4 and 6 weeks for evaluation and further photographs.

The additional 6 patients were entered into a separate protocol to determine the possibility of the topical agent decreasing the appearance of spider veins of the face according to the following protocol:

1. Apply Cream A with the right hand to the right side of the face and Cream B to the left side of the face with the left hand at bedtime on dry skin.

2. Wash hands immediately after application.

3. Use no Retin A, glycolic acid or moisturizers during the study.

4. Return in 2,4 and 6 weeks for photographs.

Within 4 weeks of application, all patients with actinic purpura and easy bruising had a decrease in the time required for healing on the active compound side compared to the opposite (placebo) side as well as a decreased appearance of lesions following trauma. No patients reported adverse effects of the active cream or the placebo-no itching, erythema, dryness, etc. Two patients noticed a decrease in the lentigines on the active side versus the placebo side, which was also evident in the photographs. There was no difference in the spider veins of the face in any of the patients comparing the active to the placebo agent.

Figure 2:
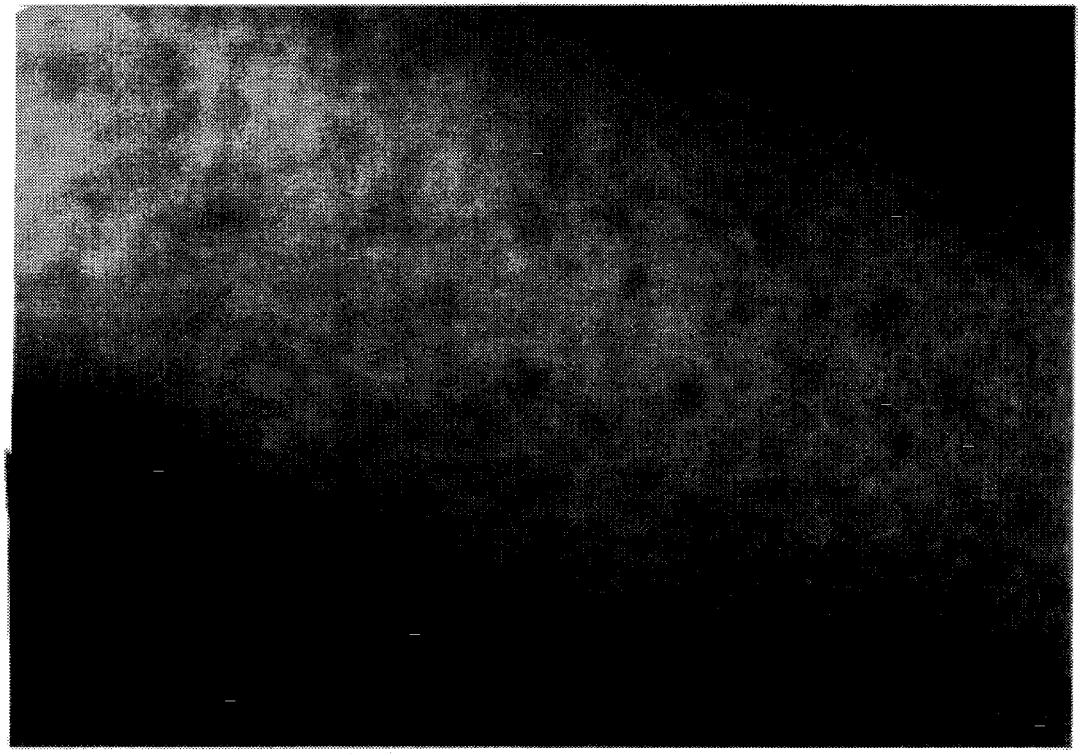
FIG. 2 is a photograph of iatrogenic purpura on a patient's right arm after two days of treatment with 0.8% to 1% vitamin K-1 cream.
Figure 3:
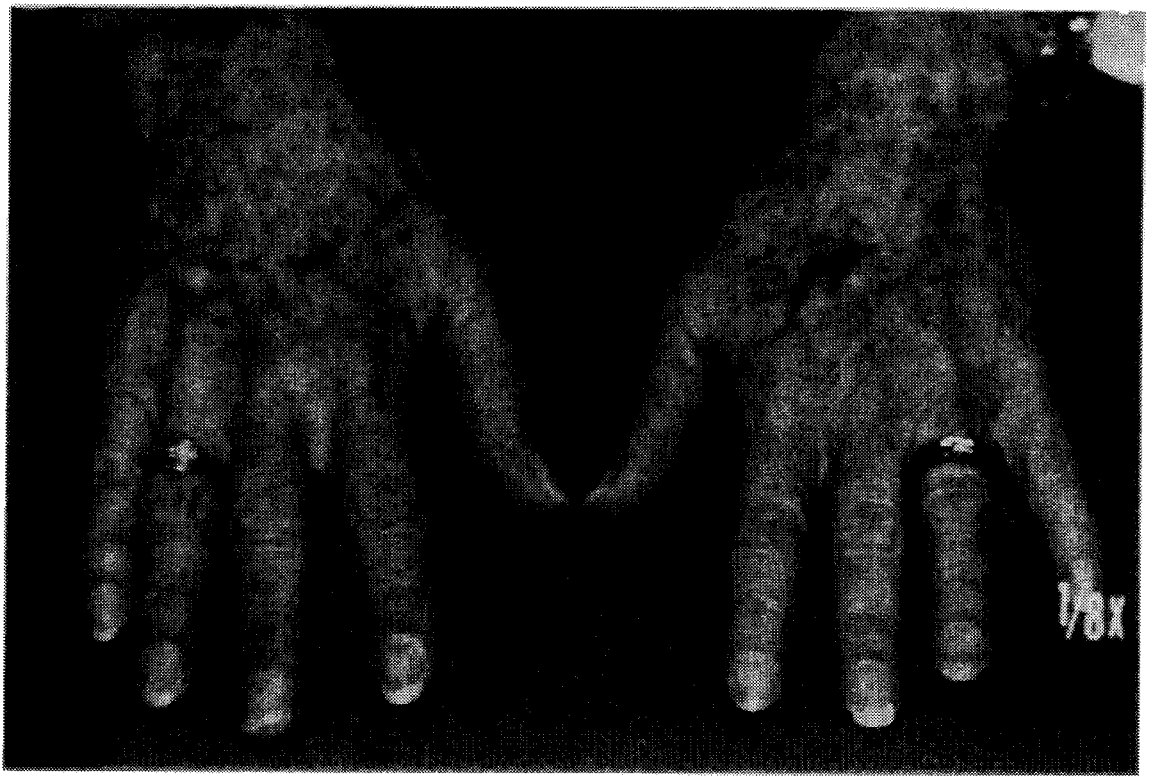
FIG. 3 is a photograph of actinic purpura and lentigines on a patient's hands before treatment with 0.8% to 1% vitamin K-1 cream.
Figure 4:
FIG. 4 is a photograph of a patient's right hand before treatment with 0.8% to 1% vitamin K-1 cream.
Figure 5:
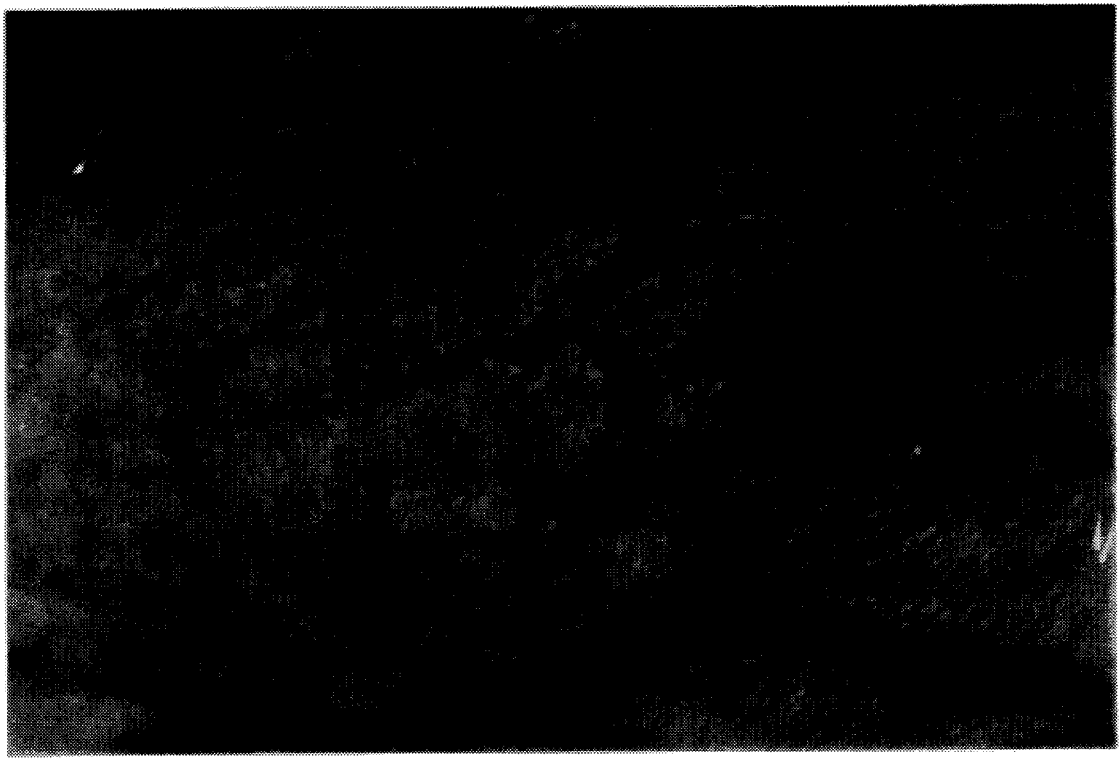
FIG. 5 is a photograph of a patient's right hand after four weeks of treatment with 0.8% to 1% vitamin K-1 cream.
Figure 6:
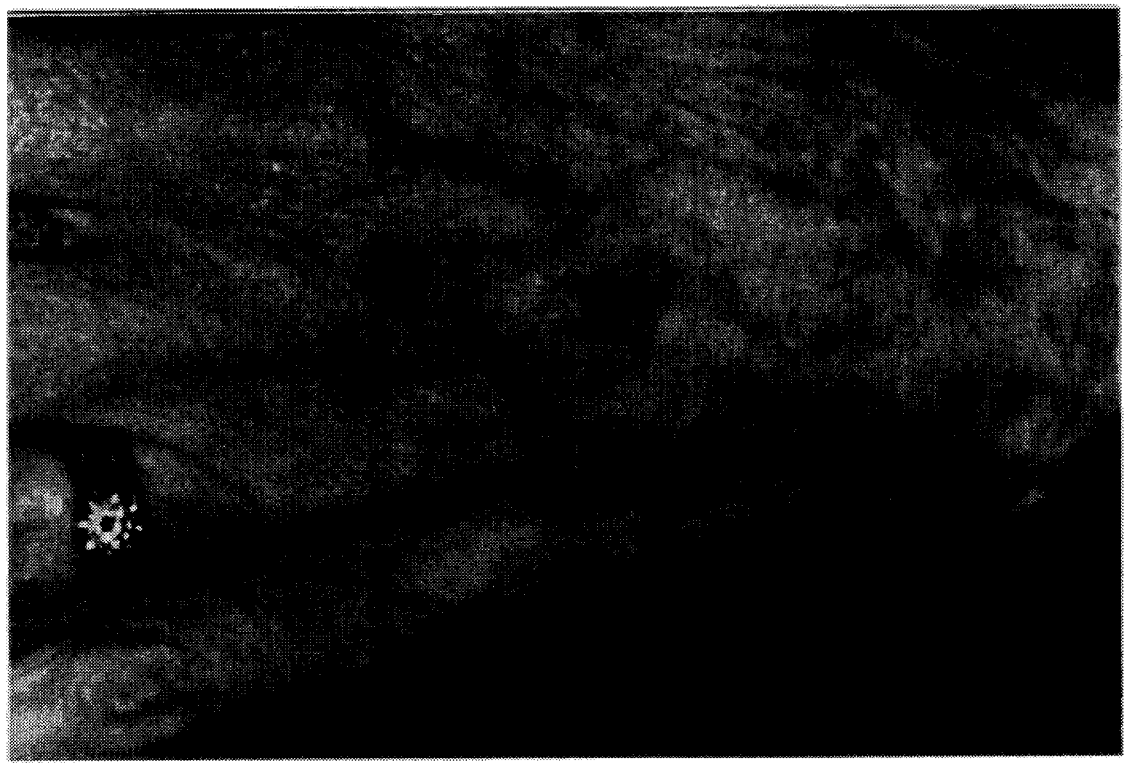
FIG. 6 is a photograph of a patient's left hand before treatment.
Figure 7:
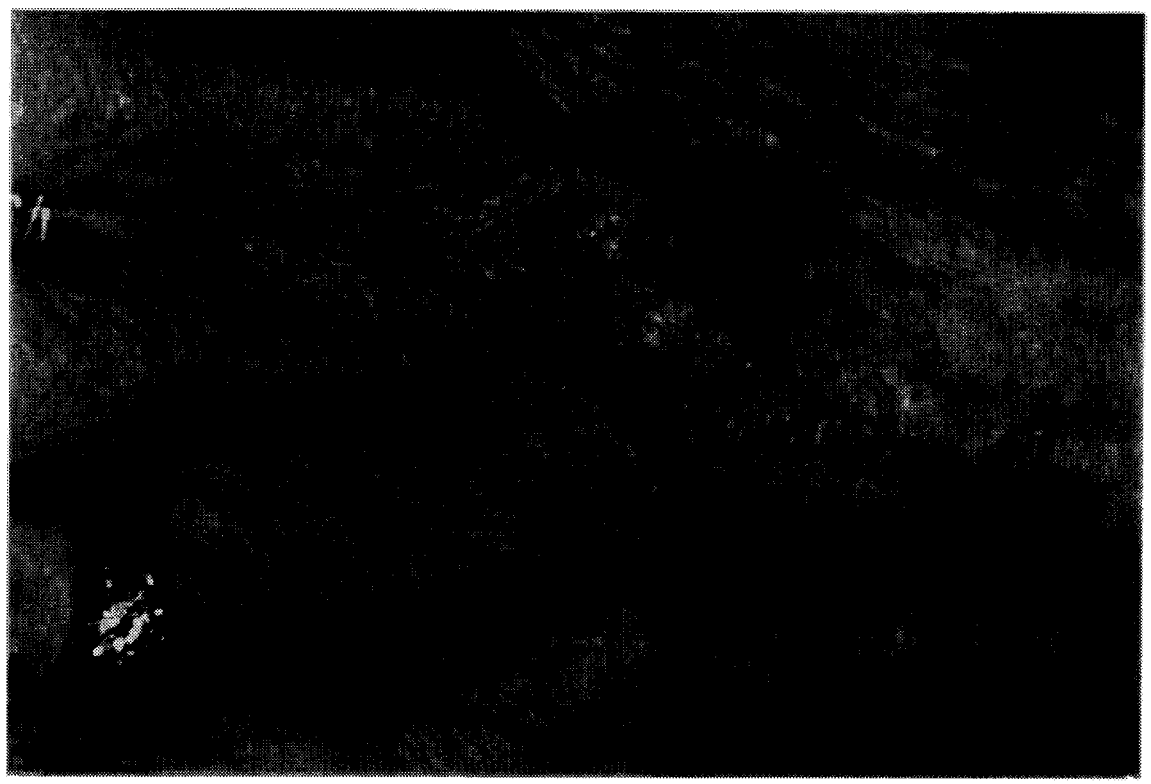
FIG. 7 is a photograph of a patient's left hand after four weeks of treatment with a placebo.

The comparative results are shown in the attached drawings (photographs) where FIG. 2 shows the effect of two days before treatment with 0.8% to 1% vitamin K-1 cream in comparison to FIG. 1 which shows iatrogenic purpura prior to treatment. FIGS. 3, 4 and 6 show blood vessel disorders of the skin and disorders of the skin caused by photoaging before treatment. FIG. 5 shows the effect of four weeks of treatment with 0.8% to 1% vitamin K-1 cream on a patient's right hand. In contrast, FIG. 7 shows the effect on a patient's left hand after four weeks of treatment with a placebo.

CASE STUDY OF TREATMENT WITH VITAMIN K-1 CREAM-5%

A case study of the effects of a vitamin K-1 cream-5% used in treatment of blood vessel disorders of the skin and skin disorders caused by photoaging involve the use of a vitamin K-1 cream having a 5% concentration of vitamin K-1 on five patients. The patients exhibited blood vessel disorders on certain areas of the body. The disorders had been caused by either trauma, surgery or sun damage. Two creams were prepared, one with vitamin K-1 (5%) and one identical except with no vitamin K and added yellow color to make the agents appear the same. Because of the size of the vitamin K molecule, it was necessary to develop a unique delivery system to ensure penetration.

At the commencement of this study, patients were evaluated and photographed. Informed consent was obtained from the patients. Patients were instructed according to the following protocol:

1. Apply Cream A with the right hand to the right side of the face and Cream B to the left side of the face with the left hand at bedtime on dry skin.

2. Wash hands immediately after application.

3. Use no Retin A, glycolic acid or moisturizers during the study.

4. Return in 2,4 and 6 weeks for photographs.

Three out of the five patients showed a decrease in the appearance of true blood vessels following application of the vitamin K-1 cream-5%. In addition, the vitamin K-1 cream-5% was applied to blood vessel disorders on the legs. However, no improvement of blood vessel disorders located on the legs were observed.

While there have been described particular embodiments of the present invention of a new and useful formulation of and method of using a vitamin K cream in topical therapy for the treatment of blood vessel disorders of the skin, it is not intended that such references be construed as limitations upon the scope of this invention except as set for the in the following claims. Further, although there have been described certain quantities and proportions used in the formulation of the preferred embodiments, it is not intended that such quantities and proportions be construed as limitations upon the scope of this invention except as set further in the following claims.

REFERENCES

Guillamoont, Sann et al. (1993). *J. Pediatr. Gastroenterology and Nutr.*, Jan. 16 (1). pp. 10–14.

Beeson, P., McDermott, W. (1967). *Textbook of Medicine.*, W. B. Saunders Co, Philadelphia. pp. 1135–1136.

Solomons, T. (1992) *Organic Chemistry.* John Wiley and Sons, Inc., New York. 5th ed., p. 951.

Dam K. H. (1929). *Biochem. Z.* 215, 475.

Dam K. H., et al, (1939) *Helv. Chim. Acta.* 22, 310.

Structure: MacCorquodale D. W., Cheney L. C. et al., (1939) *J. Biol. Chem.* 131, 357.

Fieser L. F., *J. Am. Chem. Soc.* 61, 3467.

Early syntheses: Almquist, H. J., Klose, A. A., (1939) *J. Am. Chem. Soc.* 61, 2557.

Binkley, S. B., et al., ibid. 2558.

Feiser, L. F., ibid. 2559.

Mayer, M., et al., (1964) *Helv. Chim. Acta.* 47, 221.

Jackman, L. M., et al., (1965) ibid. 48, 1332.

Sato et al., *Chem. Commun.* 1972, 953.

*J. Chem. Soc. Perkin Trans. 1* 1973, 2289.

Tachibana Y., *Chem. Letters.* 1977, 901.

Shearer, M. J., et al., (1970) *Brit. J. Haematol.* 18, 297; (1972) 22, 579.

Matschiner, J. T., et al., (1972) *J. Nutr.* 102, 625.

Hassan M. M. A., et al., In *Analytical Profiles of Drug Substances,* Vol. 17, K. Florey, Ed. (Academic Press, New York, 1988) pp. 449–531.

Merck and Co., Inc., Rahway, N.J., *The Merck Index,* 11th ed., 1989. pp. 1580–1581.

Medical Economics, Inc., Montvale, N.J. (1993), Aqua-MEPHYTON® (Vitamin K). *Physicians' Desk Reference* 47th ed., p.1473.

Poller L.: Laboratory Control of Anticoagulant Therapy. Seminars in Thrombosis and Hemostasis; 12:1, pp 13–19, 1986. Physicians' Desk Reference 47th ed., Medical Economics, Inc., 1993.

Coumadin® *Phyisicians' Desk Reference* 47th ed., Medical Economics, Inc., Montvale, N.J., 1993. pp 963–965.

Weiss J. S., Ellis C. N., et at., JAMA 259:4. 1988.

Elson M. L. Cos Derm 5(1):12, 1992. pp 36–40.

Elson M. L. Cos Derm vol. 6, no. 7, July 1993. pp 31–32.

Braverman I. M. *Skin Signs of Systemic Disease* 2nd ed. W. B. Saunders Company, Philadelphia, Pa., 1980. p 600.

Fitzpatrick T. B., et al., *Dermatology and General Medicine* 4th ed., McGraw Hill, New York, 1993. Chapter 145-25.

Furi B.: In Rakel RD (ed) *Conn's Current Therapy.* WB Saunders, Philadelphia, Pa., 1993. pp 564–565.

What I claim is:

1. A method of treating blood vessel disorders of the skin and skin disorders caused by photo-aging comprising:

a) coformulating a pharmaceutical composition wherein said composition contains from 0.01% to 50% vitamin K;

b) applying said pharmaceutical composition topically to treat blood vessel disorders of the skin and skin disorders caused by photoaging, wherein said blood vessel disorders of the skin and skin disorders caused by photo-aging does not include spider veins.

2. The method of treating blood vessel disorders of the skin and skin disorders caused by photoaging as in claim 1, wherein the method comprises:

a) coformulating a pharmaceutical composition comprising a form of vitamin K in combination with a plurality of substituents selected from the group consisting of: ethyl alcohol, isopropyl alcohol, benzyl alcohol, isopropyl palmitate, lecithin soya granular, Pluronic F-127 NF, methyl paraben, propyl paraben, Dowicil 200, and water; and b) applying said pharmaceutical composition topically to treat said blood vessel disorders of the skin and skin disorders caused by photoaging.

3. The method of treating blood vessel disorders of the skin and skin disorders caused by photoaging as in claim 1, wherein said pharmaceutical composition includes substantially: 5 grams of vitamin K-1 (Phytonadione), 5 ml 95% ethyl alcohol SD40, 2 ml benzyl alcohol, 10 grams lecithin granules, 10 ml isopropyl palmitate NF, 20 grams Pluronic F-127 NF, and preserved water is added to QS said composition to 100 grams.

4. The method of treating blood vessel disorders of the skin and skin disorders caused by photoaging as in claim 1, wherein said pharmaceutical composition includes substantially: 1 gram vitamin K-1 (Phytonadione), 2.42 ml of 99% isopropyl alcohol, 1.73 ml of benzyl alcohol, 8.26 grams of lecithin granules, 7.44 ml of isopropyl palmitate NF, and 16.53 grams Pluronic F-127, NF, 0.04 gram propyl paraben, 0.13 gram methyl paraben, 0.04 gram Dowicil 200 and 62.41 ml distilled water.

5. The method of treating blood vessel disorders of the skin and skin disorders caused by photoaging as in claim 1, wherein the form of vitamin K used in said pharmaceutical composition is selected from the group consisting of vitamin K-1, vitamin K-2 and synthetic vitamin K analogs.

6. A method of treating blood vessel disorders of the skin and skin disorders caused by photo-aging comprising:

a) coformulating a pharmaceutical composition wherein said composition contains from 0.01% to 50% vitamin K;

b) applying said pharmaceutical composition topically to treat blood vessel disorders of the skin and skin disorders caused by photoaging selected from the group consisting of bruising, actinic purpura, iatrogenic purpura and lentigines.

7. The method according to claim 6 wherein said pharmaceutical composition further comprises a plurality of substituents selected from the group consisting of: ethyl alcohol, isopropyl alcohol, benzyl alcohol, isopropyl palmitate, lecithin soya granular, Pluronic F-127 NF, methyl paraben, propyl paraben, Dowicil 200 and water.

8. The method according to claim 6 wherein the form of vitamin K used in said pharmaceutical composition is selected from the group consisting of vitamin K-1, vitamin K-2 and synthetic vitamin K analogs.

* * * * *